(12) United States Patent
Zahedi et al.

(10) Patent No.: US 6,719,806 B1
(45) Date of Patent: Apr. 13, 2004

(54) LOWER LIMB PROSTHESIS AND CONTROL UNIT

(75) Inventors: Mir Saeed Zahedi, Guildford (GB); Andrew John Sykes, Camberley (GB)

(73) Assignee: Chas. A. Blatchford & Sons Limited (GB)

( * ) Notice: Subject to any disclaimer, the term of this patent is extended or adjusted under 35 U.S.C. 154(b) by 0 days.

(21) Appl. No.: 09/623,790

(22) PCT Filed: Mar. 3, 1999

(86) PCT No.: PCT/GB99/00640

§ 371 (c)(1),
(2), (4) Date: Oct. 26, 2000

(87) PCT Pub. No.: WO99/44547

PCT Pub. Date: Sep. 10, 1999

(30) Foreign Application Priority Data

Mar. 4, 1998 (GB) .............................................. 9804611

(51) Int. Cl.⁷ .............................. A61F 2/48; A61F 2/62
(52) U.S. Cl. .......................................... 623/24; 623/39
(58) Field of Search .............................. 623/24, 39, 40, 623/41, 42, 43, 44

(56) References Cited

U.S. PATENT DOCUMENTS 5,133,774 A * 7/1992 Sawamura et al. ........... 623/24
5,571,205 A * 11/1996 James .......................... 623/24
5,893,891 A * 4/1999 Zahedi ......................... 623/24
6,113,642 A * 9/2000 Petrofsky et al. ............. 623/24

FOREIGN PATENT DOCUMENTS

| EP | 0 549 855 A2 | 7/1993 | ............. A61F/2/64 |
| GB | 2 280 609 | 2/1995 | ............. A61F/2/68 |
| WO | WO 96/41599 | 12/1996 | ............. A61F/2/68 |

OTHER PUBLICATIONS

M.S. Zahedi et al, "Repeatability of kinetic and kinematic measurements in gait studies . . . ".

Prosthetics and Orthotics Intl., 1987, 11, 55–64.

* cited by examiner

Primary Examiner—Corrine McDermott
Assistant Examiner—William H. Matthews
(74) Attorney, Agent, or Firm—Hale and Dorr LLP

(57) ABSTRACT

A lower limb prosthesis for an above-knee amputee that includes a dynamically adjustable knee movement control unit arranged to control flexion and/or extension of a knee joint of the prosthesis automatically in response to a sensed step-to-step variability of at least one kinetic or kinematic parameter of locomotion in order to reduce the step-to-step variability.

23 Claims, 2 Drawing Sheets

LOWER LIMB PROSTHESIS AND CONTROL UNIT

CROSS REFERENCE TO RELATED APPLICATIONS

This application is a U.S. national phase application filed under U.S.C. 371 of International Application No. PCT/GB99/00640, filed Mar. 3, 1999, which was published under PCT Article 21(2) in English. International Application No. PCT/GB99/00640 claims priority from United Kingdom Application No. 9804611.3, filed Mar. 4, 1998.

This invention relates to a lower limb prosthesis including a dynamically adjustable joint movement control unit arranged to control either or both of flexion and extension of the joint automatically.

It is known from British Patent Application No. 2280609A to provide a lower limb prosthesis with a dynamically adjusting control system for controlling the movement of a shin part of the prosthesis about a knee axis on a thigh part of the prosthesis according to the amputee's speed of locomotion. A pneumatic piston and cylinder device coupled between the thigh part and the shin part has a motor-driven valve which alters the resistance of the device to movement at the knee joint in response to command signals from an electronic control circuit deriving input signals from a transducer mounted on the control device, the repetition rate of the input signals being representative of the speed of locomotion, particularly the step period during walking.

The control circuit includes a radio receiver for receiving command signals from a remote control transmitter operated by a prosthetist, a processor for processing the command signals and the transducer signals, and a memory for storing a map of valve settings against locomotion speed ranges. The processor has a teaching mode whereby the amputee is asked to walk at a particular speed and the system is "taught" by the prosthetist inasmuch as the prosthetist causes the valve to be adjusted under remote control in real time while the amputee is walking until the best gait is obtained. The same process is performed at different walking speeds and the prosthetist selects a valve setting for each speed which, in his or her opinion, appears to produce the best walking gait. These valve settings are stored at the end of a teaching session. In a playback mode of the processor, signals corresponding to the stored valve settings are fed to the motor-driven valve automatically according to the speed at which the amputee walks.

The above system has yielded notable improvements in gait for above-knee amputees due to its adaptation of resistance to knee joint movement to different settings suiting different walking speeds rather than relying on a fixed resistance setting for all walking speeds. These improvements have been achieved without requiring excessively lengthy sessions with the prosthetist.

The field of gait analysis in general has received considerable attention over the years. In "Repeatability of Kinetic and Kinematic Measurements in Gait Studies of the Lower Limb Amputee" by Zahedi et al in Prosthetics and Orthotics International, 1987, 11, 55–64, a computational method is disclosed for performing gait measurements which are useful in biomechanical evaluation. One of the observations arising out of this work is that small differences in the geometric alignment of a lower prosthesis influence the degree of repeatability and pattern of load actions. It is also suggested that, from biomechanical considerations, alignments which have the least variation in loads from step to step in antero-posterior bending moment and axial loading parameters may be nearer to an optimum condition.

According to a first aspect of this invention, there is provided a lower limb prosthesis which automatically reacts to a variability measurement dynamically to adjust a control device which forms part of the prosthesis and which affects the flexion and/or the extension of a joint connecting different parts of the prosthesis. In this way, it is possible to provide a self-learning adaptive control system for a lower limb prosthesis, the system measuring the variation of one or more parameters associated with the dynamic operation of the limb, and automatically processing the variation measurement to optimize or reduce the variability of the parameter, preferably using an iterative process, in order to achieve an optimum locomotion characteristic.

The system is primarily applicable to a lower limb prosthesis for an above-knee amputee, the control device being a knee flexion control device such as a piston and cylinder assembly having an electrically adjustable valve responsive to an adjusting signal generated by a microprocessor which is programmed to derive a kinematic parameter variability value from input signals produced by a transducer mounted on the limb.

The kinematic parameter may be the amplitude of the flexion angle of the joint which, in the case of flexion and/or extension of the joint being controlled by a piston and cylinder device connected between a side part of a shin part of the prosthesis, may be represented by the amplitude or magnitude of the piston stroke. Alternatively or in addition, the duration of the flexed state (e.g. the time interval from commencement of the flexion movement to termination of the extension movement, these points typically being determined by setting angular thresholds or piston positional thresholds) may be used as another kinematic parameter, preferably as a proportion of the total step period. As a further alternative, stride length may be used as a kinematic parameter.

According to a second aspect of the invention, there is provided a lower limb prosthesis for an above-knee amputee, the prosthesis including a dynamically adjustable knee movement control unit arranged to control flexion and/or extension of a knee joint of the prosthesis automatically in response to the sensed step to step variability of at least one kinetic or kinematic parameter of locomotion in order to reduce the said step to step variability. Typically, the sensed variability is an electrical signal value representative of the degree of variation of a kinematic parameter measured during each of a plurality of steps taken by the amputee during locomotion, the parameter being measured during each step taken by the amputee which is within a predetermined range of locomotion, such as a particular walking speed range or a particular category of locomotion. In this context "category of locomotion" means different modes of locomotion such as walking on a level surface, walking down an incline, walking up an incline, walking down stairs, climbing up stairs, or running. Speeds of walking or running as speed ranges may be determined by measuring the repetition rate or the average step period of a walking or running cycle, each cycle extending, for instance, from heel contact to heel contact through stance phase and swing phase.

The control system may be configured to determine the variability of one or more kinetic or kinematic parameters over each of a plurality of the ranges of locomotion so that the control device is adjusted to a plurality of optimum settings for the different respective locomotion ranges. It is possible, then, for the system to determine the range of locomotion from received electrical signals from one or more transducers forming part of the prosthesis, and, using the same signals, to perform an iterative variability measurement and adjustment process within each respective locomotion range. The process minimizes variability of the selected parameter or, in the case of the variability of a plurality of parameters being measured, minimizes the variability of at least one of them (which is designated the primary parameter). Generally, altering or minimizing the variability of a kinematic parameter is associated with altering or minimizing an underlying kinetic parameter of locomotion.

According to a third aspect of the invention, a lower limb prosthesis includes a dynamically adjustable control device for controlling movement of the prosthesis during locomotion, a transducer for generating a sensing signal related to a kinematic parameter of locomotion, and an electronic control circuit having an input coupled to the transducer and an output coupled to the control device, wherein the transducer and the control circuit are configured to determine the variability of the kinematic parameter and to generate output signals for adjusting the control device thereby to reduce the variability of the parameter. In the preferred prosthesis, the control circuit is configured to record a value of the kinematic parameter during each of a plurality of locomotion cycles, to compare the recorded values to establish a variability measurement, to compare the variability measurement with a reference variability value and, if the variability measurement exceeds the reference value, to initiate a control device adjustment procedure in which the control device is dynamically adjusted so as substantially to minimize the variability of the or each parameter.

From a method aspect, the preferred control system measures the speed of walking, computes the variation of a kinematic parameter over a number of steps, processes the measured parameter data in order to determine whether the degree of variation falls within a band of optimum parameter variation, adjusts the resistance to joint flexion and/or extension by a predetermined increment in accordance with the degree of variation of the parameter or parameters in order to reduce the amount of variability. The corresponding control device settings, in conjunction with walking speed values, can be stored in order that, in a playback mode, the control device is adjusted to a variability-minimizing setting corresponding to a measured walking speed as determined by the stored relationships.

The optimization process may be carried out continuously during use of the prosthesis, variation of the kinematic parameters being iteratively reduced whenever the variability deviates from a predetermined optimum condition. The speed of walking may be defined according to a number of non-overlapping speed ranges which might be designated "slow", "medium", and "fast", the stored data associating a limb control device setting for each range which has been determined by means of the automatic self-learning process as yielding substantially the minimum variation in the kinematic parameter or parameters.

The invention will now be described by way of example with reference to the drawings in which.

Figure 1:
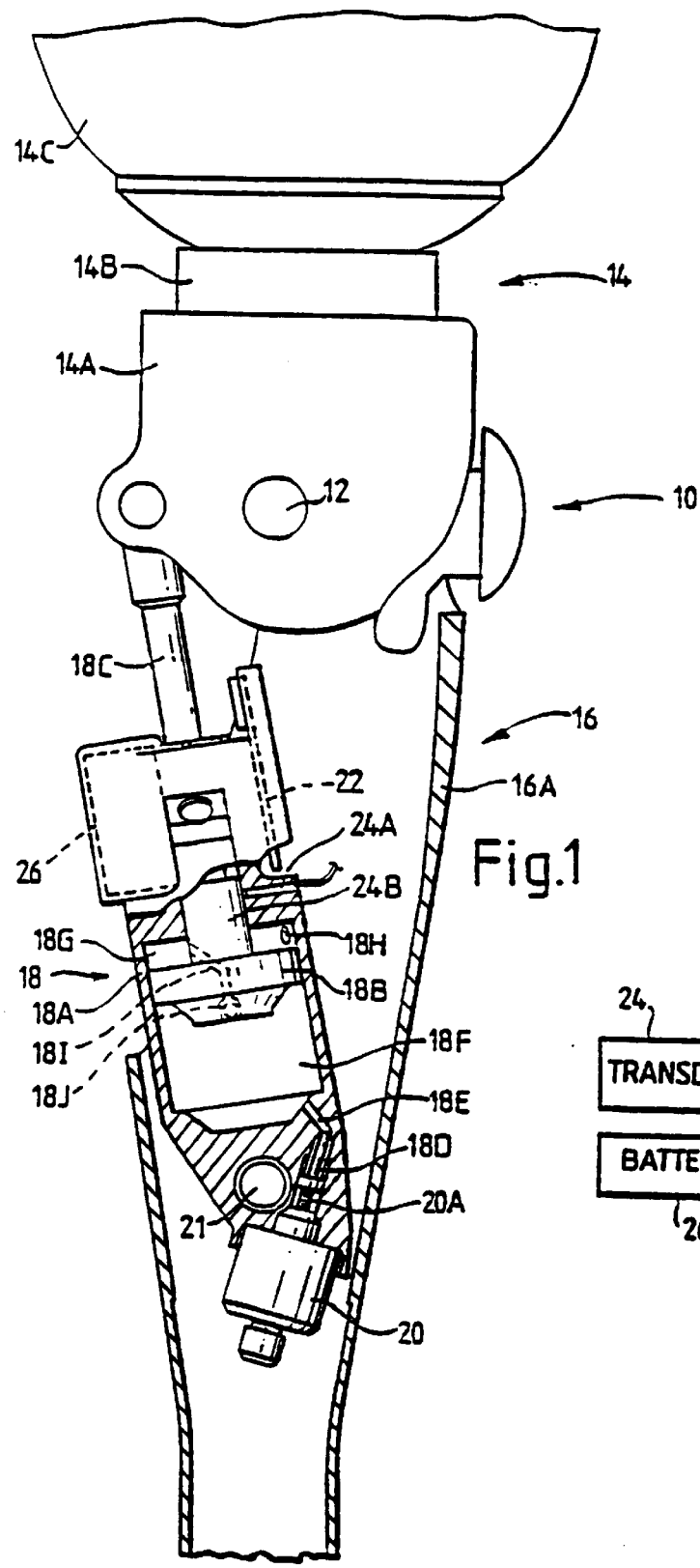
FIG. 1 is a partly sectioned side elevation of part of a lower limb prosthesis incorporating a flexion control device and electronic control elements.

A lower limb prosthesis in accordance with the invention is shown in FIG. 1. The prosthesis has a knee joint 10 with a knee pivot 12 connecting a thigh component 14 to a shin component 16. The thigh component comprises a knee chassis 14A, an alignment device 14B, and a stump socket 14C. The shin component 16 has a conventional carbon fibre reinforced plastics shin cradle 16A which houses a piston and cylinder assembly 18 acting as a flexion control device to form part of a control system. The assembly 18 comprises a cylinder 18A which is pivotally coupled to the posterior part of the shin cradle 16A, and a piston 18B having a piston rod 18C which is pivotally coupled to the knee chassis 14A. The piston and cylinder assembly 18 is a pneumatic device, the resistance to flexion of the knee joint being controlled by a needle valve 18D which is adjustable by an electrical stepper motor 20 and an associated screw-threaded shaft 20A connected to the needle member of the needle valve. A d.c. motor may be used as an alternative to a stepper motor. The needle valve 18D lies in a passage 18E in the body of the cylinder 18A, the passage 18E interconnecting the cylinder interior spaces 18F, 18G on opposite sides of the piston 18C and emerging at a port 18H in the wall of the cylinder. Operation of the motor 20 causes the shaft 20A to move axially so that the needle member moves into or out of a passageway forming part of passage 18E.

The passage 18E constitutes a first bypass passage interconnecting the cylinder spaces on opposite sides of the piston 18C. A second bypass passage 18I incorporating a valve such as a one-way valve 18J is formed in the piston 18C so that the needle valve 18D is effective only on one stroke of the piston, in this case the stroke corresponding to increasing flexion of the knee joint 10. The one-way valve 18J may be arranged so as not to close-off the second bypass passage 18I completely on the increasing flexion stroke, but rather merely to reduce the orifice area through the piston 18C. Such an arrangement has the effect of the needle valve 18D determining the resistance to motion of the piston 18C in both directions, i.e. for increasing and decreasing flexion, but with the effect of variations in the orifice area of the needle valve 18D being greater in one direction than the other, depending on the direction of operation of the valve 18J.

It is also possible to include a one way valve in the passage communicating with port 18H. The stepper motor 20 and its threaded shaft 20A are mounted in the body of the cylinder 18, preferably adjacent the pivotal coupling 21 of the cylinder 18 to the shin 16.

The stepper motor is driven by a microcomputer which forms part of an electronic circuit assembly 22 and is part of the control system. The microcomputer determines knee flexion and extension movements by means of a magnetic proximity sensor comprising a first part, preferably a transducer 24A, mounted in or associated with the cylinder body 18A, and a second part, preferably a permanent magnet 24B, mounted on or associated with the piston 18B. As an alternative, for instance, transducer 24A may be mounted on a printed circuit board constituting the electronic circuit assembly 22 which is, in turn, associated with cylinder 18. The electronic circuit assembly 22 and the stepper motor 20 are powered by batteries, one of which is shown in FIG. 1 and indicated by the reference 26.

Figure 2:
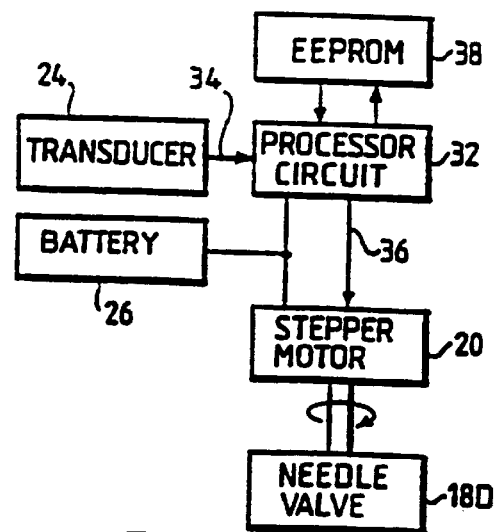
FIG. 2 is a block diagram of a prosthesis control system in accordance with the invention.

The electronic circuit assembly 22 is shown in more detail in FIG. 2. More particularly, the circuitry comprises a processor circuit 32 which receives transducer signals via input 34 and controls the stepper motor 20 via output 36. A non-volatile memory in the form of an EEPROM 38 stores walking speed and valve setting data produced by the processor circuit 32, and writes such data to the processor circuit 32 when required.

The processor circuit 32 includes an output driver for driving the stepper motor 20 which in turn moves the needle valve 18D, and it has an input for receiving signals from the flexion sensor 24 comprising transducer 24A and magnet 24B (See FIG. 1).

Operation of the processor circuit 32 in accordance with an internally stored program will now be described with reference to FIG. 3. This program offers automatic setting of the control device valve ("automatic programming") without intervention by a prosthetist, but manual programming by the prosthetist using a remote control unit as described in the above-mentioned British Patent Application No. 2280609A can be performed as an alternative to or in conjunction with automatic programming using additional software stored in the electronic circuitry 22.

It must be understood, firstly, that the signals received from transducer 24A can be interpreted by measuring their width, magnitude, and repetition rate to derive values for the step period (the reciprocal of the waling speed), the stroke magnitude, and stroke duration, the last of these being representative of the time taken to complete the swing phase relative to the complete step period. These three variables are designated T, ISI, and $T_S$ in FIG. 3. The stroke magnitude and stroke duration are kinematic parameters, the variability of which is assessed in order to obtain an optimum setting of the swing phase resistance offered by piston and cylinder assembly 18 in each of five different walking speed ranges (represented in FIG. 3 by step period ranges $T_1$ to $T_5$). Different numbers of walking speed ranges may be used. The variability measurements $\Delta$ISI and $\Delta T_S$ are determined by comparing the stroke magnitude and stroke duration measurements over a number of consecutive steps, here seven steps, for which T remains within one of the ranges $T_1$ to $T_5$. According to whether these variability values $\Delta$ISI and $\Delta T_S$ exceed predetermined thresholds $A_i$, $2A_i$, $B_i$, and $2B_i$ respectively, the valve 18D is adjusted in order to reduce the variability measurements below the thresholds.

Looking at this in more detail, the sequence of operations carried out by the processor circuit 32 begins with selecting either manual programming or automatic programming and selecting either pre-programmed variability values or previously determined variability values $\Delta$ISI and $\Delta T_S$ as a starting set of values for different walking speed ranges. With manual programming the remote control unit referred to in the prior patent application mentioned above is used to send command signals for appropriate valve adjustment and for producing average walking speed values. The pre-programmed variability values may be factory set to give a starting point for automatic programming. In some circumstances, if very large variability values are measured, automatic programming may be preceded by manual programming by the prosthetist and reading the previous values of stroke magnitude and stroke duration for each speed range $T_1$ to $T_5$ stored in EPROM 38 (program element 50). If adjustment programming is selected (program element 52), and the amputee is walking, the step period, stroke magnitude and stroke duration are measured for each walking step (element 54), and for each walking step the value of the step period T is checked against corresponding limit values of the ranges $T_1$ to $T_5$ to determine whether the step being measured is within the same step period range as the previous step (element 56). If it is not, the new step period range is set (element 58) and the program returns to element 54 to measure and store T, $\Delta$ISI and $T_S$ for the next walking step.

Figure 3:
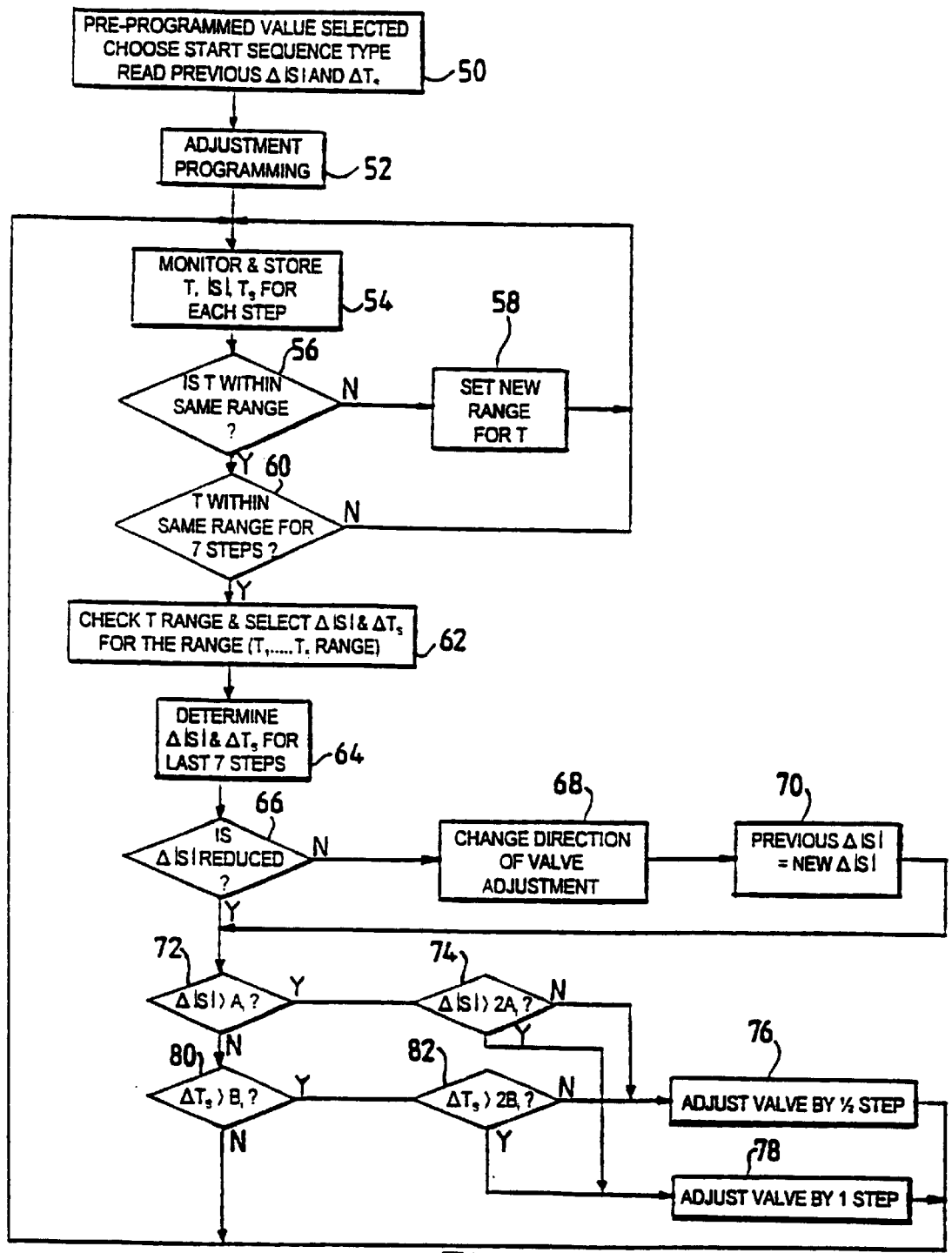
FIG. 3 is a flow chart illustrating a preferred sequence of operations performed by the control system.

If, on the other hand, the step period of the measured step is within the same step period range as the previous step, a counter is incremented (not shown) and the program returns to element 54 to run through the above described sequence again until seven consecutive steps have taken place all within one step period range, as determined by program element 60 in FIG. 3.

In element 62, the step period range is checked and the step magnitude variability and step duration variability are selected and calculated for the respective seven steps (elements 62 and 64 of the program).

Then the stroke magnitude variability is compared with the previous value (element 66). If the variability has increased, it is assumed that the last adjustment of valve 18D (FIG. 1) in the relevant step period range was in the wrong direction, and the register setting the direction of valve adjustment is updated to reverse the adjustment direction (element 68) and the previous stroke magnitude variability value is overwritten with the new stroke magnitude variability value (element 70).

Next, the measured stroke magnitude variability value is compared with a first variability threshold $A_i$ (element 72) and if that threshold is exceeded, another comparison is carried out in step 74 to determine whether the variability value exceeds a higher second variability threshold, in this case double the previous threshold, i.e. $2A_i$ (element 74). The outcome of program elements 72 and 74 is that if the stroke magnitude variability is below the first threshold $A_i$, no valve adjustment occurs. If it is between the first and second thresholds $A_i$ and $2A_i$, the valve is adjusted by half a step of the stepper motor 20 (see FIG. 1) in the direction set in the valve adjustment direction register (program element 76). If, however, the stroke magnitude variability is greater than the second threshold $2A_i$, the valve is adjusted by one stepper motor step (element 78) in the indicated direction. If the stroke magnitude variability is within the lower of the two stroke magnitude variability thresholds, as determined by program element 72, the variability of the stroke duration is assessed as a secondary variability measure. Thus, in program element 80, the stroke duration variability $\Delta T_S$ is compared against a stroke duration variability threshold $B_i$ and, if necessary, against a second stroke duration variability threshold $2B_i$ (in program element 82). Again, depending on the results of these comparisons, the valve 18D is adjusted by half a step or one step in the register—indicated direction, or no adjustment occurs.

The above-described program elements 54 to 82 form one iteration in an iterative procedure for optimally adjusting valve 18D so as to bring at least the stroke magnitude variability within the lower of its respective threshold ($A_i$). Accordingly, the next time seven steps are completed within the same step period range, the next iteration occurs, and so on until an optimum valve adjustment is obtained. The same process is carried out for other step period ranges.

It will be appreciated that adjustment of the valve may yield a decrease in one of the variability values and an increase in the other. Selection of stroke magnitude variability as the primary variability parameter ensures that reduction of stroke magnitude variability takes precedence over reduction of stroke duration variability. As an option, not shown in FIG. 3, stroke duration may be adopted as the primary variability measure, the stroke magnitude variability then becoming the secondary variability measure.

The above-described program operations can be activated by operating a switch or on detection of a special sequence of movements of the prosthesis, or it may be performed continuously during normal use of the prosthesis. The effect of the operation is that adjustment of the control device may be carried out automatically without intervention from a prosthetist. After an initial geometric alignment of the limb and, generally, an approximate adjustment of the control device, the fine adjustment of the control device is a self-teaching automatic procedure.

What is claimed is:

1. A lower limb prosthesis for an above-knee amputee, the prosthesis including a dynamically adjustable knee movement control unit arranged to control flexion and/or extension of a knee joint of the prosthesis automatically in response to a sensed step-to-step variability of at least one kinetic or kinematic parameter of locomotion in order to reduce the degree of variation between different values of the at least one kinetic or kinematic parameter associated with different respective steps taken by the amputee during locomotion.

2. A prosthesis according to claim 1, wherein the sensed step-to-step variability comprises an electrical signal value representative of the degree of variation of the at least one kinetic or kinematic parameter measured during each of a plurality of steps taken by the amputee during locomotion.

3. A prosthesis according to claim 2, wherein the at least one kinetic or kinematic parameter comprises the magnitude of knee joint flexion during each of said steps taken by the amputee within a predetermined range of locomotion.

4. A prosthesis according to claim 3, wherein the range of locomotion is a speed range.

5. A prosthesis according to claim 3, wherein the control unit comprises
 a variable damper device coupled to upper and lower limb components which move relative to each other during flexion and extension of the knee joint,
 a transducer associated with the damper for generating an electrical transducer output signal representative of the relative position of relatively movable parts of the damper, and
 an electronic control circuit for processing the transducer output signal so as to generate a signal value indicative of the step-to-step variability of the at least one kinetic or kinematic parameter sensed over a plurality of steps taken by the amputee, and to feed an adjusting signal to the damper device to adjust the damping of the knee joint in response to the signal value indicative of the step-to-step variability exceeding at least one preset threshold value.

6. A prosthesis according to claim 1, wherein the control unit is arranged to perform an iterative process of repeated variability sensing and control unit adjusting in order to progressively reduce the variability of the at least one kinetic or kinematic parameter substantially to a minimum.

7. A prosthesis according to claim 1, wherein the control unit is configured to record a value of said at least one kinetic or kinematic parameter during each of a plurality of locomotion cycles,
 to compare the recorded values to establish a variability measurement,
 to compare the variability measurement with a reference variability value and,
 if the variability measurement exceeds the reference value, to initiate a control device adjustment procedure.

8. A prosthesis according to claim 7, wherein the control unit is configured
 to determine a range of locomotion before recording the at least one kinetic or kinematic parameter values, and
 to establish the variability measurement in respect of a plurality of the at least one kinetic or kinematic parameter values corresponding to a plurality of consecutive locomotion cycles within the range of locomotion, the control device adjustment procedure being performed during subsequent locomotion cycles within the range of locomotion.

9. A lower limb prosthesis including
 a dynamically adjustable control device for controlling movement of the prosthesis during locomotion,
 a transducer for generating a sensing signal related to a kinematic parameter of locomotion, and
 an electronic control circuit having an input coupled to the transducer and an output coupled to the control device, wherein the transducer and the control circuit are configured to determine the variability of the kinematic parameter and to generate output signals for adjusting the control device thereby to reduce the step-to-step variability of the kinematic parameter so as to obtain an optimum setting of the control device, the step-to-step variability being the degree of variation between different values of the kinematic parameter associated with different respective steps taken by the amputee during locomotion.

10. A prosthesis according to claim 9, wherein the transducer and the control circuit are configured to determine the variability of the kinematic parameter over a predetermined range of locomotion and the output signals are generated to cause the control device to be adjusted to an optimum setting at which the variability of the kinematic parameter when locomotion is within the range is substantially minimized.

11. A prosthesis according to claim 10, wherein
 the transducer and the control circuit are configured to determine the variability of the kinematic parameter over each of a plurality of predetermined ranges of locomotion, and
 the output signals are generated to cause the control device to be adjusted to a plurality of respective optimum settings, one for each range, each setting substantially minimizing variability of the kinematic parameter within the respective locomotion range.

12. A prosthesis according to claim 10, wherein the range of locomotion comprises a step period range or a range of kinematic parameter values related to step period values.

13. A prosthesis according to claim 10, wherein the range of locomotion comprises a locomotion category.

14. A prosthesis according to claim 9, wherein the kinematic parameter comprises at least one of a knee flexion angle and a parameter representative of the knee flexion angle.

15. A prosthesis according to claim 9, wherein the kinematic parameter comprises a stride length.

16. A prosthesis according to claim 15, wherein the stride length is used as a second kinematic parameter, the variability of which is determined.

17. A control system for a lower limb prosthesis comprising
 an input for connection to a transducer on the prosthesis which produces an electrical transducer signal in response to flexion or extension of a joint of the prosthesis,
 an output for connection to a dynamically adjustable control device associated with the joint for influencing the operation of the joint during locomotion, and
 a processor circuit arranged to compute, from the transducer signal received at the input, a variability value indicative of the variability of a kinetic or kinematic parameter of locomotion between different steps over a period of time and, automatically in response to the variability value fulfilling a predetermined condition or conditions, to produce an output signal causing the control device to be adjusted in a manner such as to reduce said variability of the kinetic or kinematic parameter.

18. A control system to claim 17, wherein the processor circuit is arranged to optimize the adjustment of the control device by alternately deriving the variability value and adjusting the control device in an iterative manner.

19. A method of controlling a lower limb prosthesis for an above-knee amputee comprising:

sensing a step-to-step variability of at least one kinetic or kinematic parameter of locomotion; and controlling flexion and/or extension of a knee joint of the prosthesis automatically in response to the sensing step in a manner such that said step-to-step variability is reduced, the variability being the degree of variation between different values of said at least one kinetic or kinematic parameter associated with different respective steps taken by the amputee during locomotion.

20. A method according to claim 19, wherein the sensing step comprises measuring said at least one kinetic or kinematic parameter during each of a plurality of steps taken by the amputee and computing a variability value indicative of the variability of said at least one kinetic or kinematic parameter of locomotion between different steps over a period of time, and wherein the controlling step comprises automatically adjusting a control device associated with the knee joint for variably resisting flexion and/or extension of the knee joint.

21. A method of controlling a lower limb prosthesis for an above-knee amputee comprising:

generating a signal indicative of a step-to-step variability of at least one kinetic or kinematic parameter of locomotion sensed over a plurality of steps taken by the amputee, the variability being the degree of variation between different values of the at least one kinetic or kinematic parameter associated with different respective steps taken by the amputee during locomotion;

adjusting a control device which controls flexion and/or extension of a knee joint of the prosthesis automatically in response to the signal indicative of a step-to-step variability obtained in the generating step; and repeating the generating and adjusting steps in an iterative process so as to progressively reduce said step-to-step variability substantially to a minimum.

22. A self-teaching method for a lower limb prosthesis for an above-knee amputee, the prosthesis including a dynamically adjustable knee movement control device, a transducer for producing a signal representative of a kinetic or kinematic parameter of locomotion, and a processing circuit coupled to the transducer and the control device, wherein the method comprises:

producing a transducer output signal representative of values of said kinetic or kinematic parameter during locomotion;

processing the transducer output signal in the processing circuit to generate a signal representative of a level of the step-to-step variability of said kinetic or kinematic parameter over a plurality of steps taken by the amputee;

generating an adjusting signal and feeding it to the knee movement control device to dynamically adjust the control device thereby altering the degree to which the control device affects knee joint flexion and/or extension in subsequent steps, the adjusting signal being generated in response to said signal representative of a level of the step-to-step variability such that the adjustment causes said variability to be reduced substantially to a minimum as locomotion proceeds.

23. A self-teaching lower limb prosthesis for an above-knee amputee comprising upper and lower leg components, a knee joint mechanism which interconnects the upper and lower leg components and which includes a knee movement control device, and an electronic control system comprising a transducer producing a transducer output signal representative of values of a kinetic or kinematic parameter of locomotion and a processing circuit coupled to the transducer, the processing circuit receiving the transducer output signal and, in response thereto, generating a signal representative of variability of said kinetic or kinematic parameter from step to step, wherein the knee movement control device includes an adjusting element for varying the degree to which it affects flexion and/or extension of the knee joint mechanism and wherein the processing circuit has an output connected to the adjusting element to set the control device for subsequent steps and provides to the output in response to the signal representative of variability an adjusting signal which dynamically adjusts the adjusting element so as to cause variability of said kinetic or kinematic parameter to be reduced substantially to a minimum.

* * * * *